(12) United States Patent
Lin (10) Patent No.: US 7,601,808 B2
(45) Date of Patent: Oct. 13, 2009

(54) **IMMUNOMODULATORY PROTEIN CLONED FROM *GANODERMA MICROSPORUM***

(75) Inventor: Tsai-Leng Lin, Banqiao (TW)

(73) Assignee: World Bio-Tech Alliance Corporation, Totola (VG)

( * ) Notice: Subject to any disclaimer, the term of this patent is extended or adjusted under 35 U.S.C. 154(b) by 303 days.

(21) Appl. No.: 11/365,881

(22) Filed: Mar. 2, 2006

(65) Prior Publication Data

US 2007/0207954 A1    Sep. 6, 2007

(51) Int. Cl.
C07K 14/00 (2006.01)
A23J 1/18 (2006.01)
A61K 36/06 (2006.01)

(52) U.S. Cl. ...................... 530/350; 530/371
(58) Field of Classification Search ............... None
See application file for complete search history.

(56) References Cited

U.S. PATENT DOCUMENTS 5,334,704 A    8/1994   Tsunoo et al.
2009/0042776 A1    2/2009   Ko et al.

FOREIGN PATENT DOCUMENTS

EP    288959    12/1994

OTHER PUBLICATIONS

Abaza et al., Effects of amino acid substitutions outside an antigenic site on protein binding to monoclonal antibodies of predetermined specificity obtained by peptide immunization: demonstration with region 94-100 (antigenic site 3) of myoglobin, Journal of Protein Chemistry, vol. 11, No. 5, pp. 433-444, 1992.*

Coleman, Effects of amino acid sequence changes on antibody-antigen interactions, 55th Forum in immunology : a structural view of immune recognition by antibodies, pp. 33-36, 1994.*

Pan et al., Purification and characterization of manganese superoxide dismutase from Ganoderma microsporum, Biochemistry and Molecular Biology International, vol. 42, No. 5, 1997, pp: 1035-1043.*

Shizuko Tanaka, Kerry Ko, Kohsuke Kinot, Kazuko Tsuchiya, Akio Yamashita, Akira Murasugi, Sadatoshi Sakuma, and Hajime Tsunoo, "Complete Amino Acid Sequence of an Immunomodulatory Protein, Ling Zhi-8 (LZ-8)", The Journal of Biology Chemistry, vol. 264, No. 28, pp. 16372-16377, 1989.

Shu-Mei Pan, Jr-Shin Ye, and Ruey-Shyang Hseu, "Purification and Characterization of Manganese Superoxide Dismutase From Ganoderma Microsporum", Biochemistry and Molecular Biology International, vol. 42, No. 5, pp. 1035-1043, 1997.

* cited by examiner

*Primary Examiner*—Delia M Ramirez
*Assistant Examiner*—Jae W Lee
(74) *Attorney, Agent, or Firm*—McDonnell Boehnen Hulbert & Berghoff LLP (57) ABSTRACT

An immunomodulatory protein is cloned from *Ganoderma microsporum*. Its molecular weight is 15863.79 Da. Its genome sequence and translated protein sequence are different from those protected by the known patent of glycoprotein LZ-8, which is isolated from the mycelium of *G. lucidum* and has immunomodulator effect, and its immunomodulator efficiency is better than that of LZ-8.

6 Claims, 8 Drawing Sheets

```
              10        20        30        40        50        60        70
              ....|....|....|....|....|....|....|....|....|....|....|....|....|....|
reLZ-8   EAEAEFMSDTALIFR LAWDVK KLSFDYTPNWGRGNPNNFIDTVTFPKVLTDKAYTYRVAVSGR NLGVKPS
reGMI    EAEAEFMSDTALIFT LAWNVK QLAFDYTPNWGRGRPSSFIDTVTFPTVLTDKAYTYRVVVSGK DLGVRPS 80        90       100       110       120       130       140
              ....|....|....|....|....|....|....|....|....|....|....|....|....|....|
reLZ-8   YAV ESDGSQKVNFLEYNSGYGIADTNTIQVFVVDPDTNNDFIIAQWNYLEQKLISEEDLNSAVDHHHHHH
reGMI    YAV ESDGSQKINFLEYNSGYGIADTNTIQVYVIDPDTGNNFIVAQWNYLEQKLISEEDLNSAVDHHHHHH
```

IMMUNOMODULATORY PROTEIN CLONED FROM *GANODERMA MICROSPORUM*

BACKGROUND OF THE INVENTION

1. Field of the Invention

The present invention relates to an immunomodulatory protein and its production method, and more particularly to an immunomodulatory protein cloned from *Ganoderma microsporum* with immunomodulator efficiency that is better than the immunomodulatory protein isolated from *Ganoderma lucidum*.

2. Description of the Related Art

*Ganoderma* or lingzhi, a natural herbal medicinal fungus that has been used in China since 100 AD, is belonged to Kingdom Fungi, Phylum Basidiomycota, Class Hymenomycetes, Order Aphyllophorales, Family Ganodermataceae, and Genus *Ganoderma*. There are around 300 different species of *Ganoderma*, but only a limited number of strains such as *Ganoderma lucidum*, *G. tsugae*, *G. capense*, *G. boninense*, *G. resinaceum*, *G. sinense*, *G. japonicum*, and *G. applanatum* were investigate and utilized in the field of pharmacology and clinical studies. After decades of pharmacology studies, *Ganoderma* or lingzhi was found to contain the active ingredients within its extracts that have the calming, analgesia, heart protecting, liver supporting, blood pressure lowering, lipid lowering cholesterol lowering, anti-allergic, anti-inflammation, anti-virus, anti-tumor and immunomodulation effects.

In 1971, Sasaki et al. found that the polysaccharides of *G. applanatu* existed the anti-tumor activity and the polysaccharides had become the first proven active ingredient in *Ganoderma* or lingzhi. The acting mechanism of polysaccharides was not to directly kill or suppress cancer cells but to activate the T cells and increased the ability of natural killer cells to improve immunity, and consequently indirectly express its anticancer activity. In addition, it enhanced the devouring ability of monocyte macrophage and promotes cell endocrine that was able to suppress tumor growth, such as the synthesis and release of interleukin (IL-2<L-4), interferon (IFN-γ and tumor necrosis factor (TNF-α).

Another active ingredient of *Ganoderma* or lingzhi, immunomodulatory protein, was isolated from the mycelium of *G. lucidum* by the Japanese research group and named as LZ-8 (Ling Zhi-8). LZ-8, consisting of 110 amino acids with molecular weight of 12,420 Da, were similar to the amino acid sequence and the secondary structure of the immunoglobulin heavy chain variable region. The native LZ-8, existing in the form of homodimer, has the effects of facilitating lymphocytes multiplication and suppressing systemic anaphylaxis reaction and Arthus reaction. Since there was no agglutination/hemagglutination reaction toward human red blood cells, LZ-8 has demonstrated the potential in the human medical applications. The related patents of LZ-8 include the patents of JP2032026, JP3172184 and JP5068561 that use LZ-8 as anti-HIV drug and its nucleotide sequence, as well as the patents of EP0288959B1 and U.S. Pat. No. 5,334,704 that are consisted of the LZ-8 protein characterization and used as immunosuppressive drugs. Two partial sequences of the glycoprotein of LZ-8, -Leu-Ala-Trp-Asp-Val-Lys-(SEQ ID NO:24) and -Asn-Leu-Gly-Val-Lys-Pro-Ser-Tyr-Ala-Val- (SEQ ID NO:25), were also protected by patent (U.S. Pat. No. 5,334,704).

LZ-8, like lectin, has the abilities of agglutinating cells and promoting lymphocyte multiplication. Lectin has the carbohydrate specific binding ability, and such carbohydrate specific binding characteristics allows it to bind with specific carbohydrate on cell surface to stimulate cells and to trigger the follow-up immune responses. Kino et al. discovered that LZ-8 was able to stimulate the multiplication of muridae spleen cells and prevented the Arthus reaction and systemic anaphylaxis reaction in 1989. The further research indicated that LZ-8 was able to effectively suppress the occurrences of autoimmune type-I diabetes in nonobese diabetic (NOD) mice. Furthermore, LZ-8 was able to significantly delay the repulsion time after the pancreas transplantation, comparing to other immunomodulatory drugs, CsA (cyclosporin A, a peptides derived from fungi with immunosuppressing effect) and FK506 (tacrolimus, an antibiotics secreted by soil-borne fungi with immunosuppressing effect).

Both CsA and FK506 existed potential poisoning toward pancreas, while no such poisoning was found toward pancreas for LZ-8. LZ-8, whether the experiments were done in vitro or in vivo, showed immunomodulatory activity, but the detailed mechanism was not clear. In 1991, Kino et al. found that LZ-8 was able to suppress the production of mouse antibodies and speculated that LZ-8 was able to suppress the systemic anaphylaxis reaction and Arthus reaction through blocking off the antibody production. Later, LZ-8 was found to be able to adjust the interactions among cells through controlling the molecules attached onto cell surfaces, and such interaction was not found in autoimmune disease patients.

*Ganoderma lucidum* immunomodulatory protein, LZ-8, has shown that even simple peptides has the immunomodulatory effect. Other researches also found that the immunomodulatory protein, FIP-gts (fungal immunomodulatory protein-gts), purified from the mycelium of *G. tsugae*, with molecular weight around 13 kD has the same amino acid sequence as LZ-8. FIP-gts was able to promote the proliferation of human peripheral lymphocytes and mouse spleen cells. In addition, it was able to purify immunomodulatory proteins with molecular weight around 13 kD from non-*Ganoderma* or lingzhi fungi, for example, FIP-fve from *Flammulina velutipes* and FIP-vvo from *Volvariella volvacea*. LZ-8, FIP-fve and FIP-vvo are similar to the variable region of immunoglobulin heavy chains. FIP-fve and FIP-vvo are similar to LZ-8 not only in the sequence and structure but also in the physiological activity.

The healthcare effects of medicinal fungi are well known and their active ingredients were purified or isolated bit by bit. Most of currently known effective ingredients are glucans or pentacyclic tritterpenoid compounds. However, these active ingredients cannot eliminate the interferences of peptidoglycan and proteoglycan during purification. Besides, these active ingredients are either the constituents of cell walls or the secondary metabolites and are difficult in mass production through hetero-expression system.

SUMMARY OF THE INVENTION

The main objective of the present invention is to provide an immunomodulatory protein cloned from *Ganoderma microsporum* (e.g. SEQ ID NO: 1), whose gene sequence and translated protein sequence are different from the ones of patented LZ-8 and its immunomodulator efficiency is better than that of LZ-8.

An immunomodulatory protein according to the present invention cloned from *Ganoderma microsporum* comprises the amino acid sequences of sequence listings, SEQ ID NO 2 and SEQ ID NO 3.

The molecular weight of an immunomodulatory protein with the above-mentioned immunomodulatory protein genes according to the present invention is 15863.79 Da.

The protein sequence of abovementioned immunomodulatory protein cloned from *Ganoderma microsporum* is different from the ones of patented LZ-8 so as to have better immunomodulator efficiency than that of LZ-8.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows the results of *G. tsugae* and *G. microsporum* performing PCR amplification by using LZ-8 primer (LZ8-F/LZ8-R) according to the preferred embodiment of the present invention, wherein:

The arrows in FIG. 1A indicate the used primers, wherein 3'GW-F was used in 3' genome walking;

FIG. 2 shows the 3' genome walking results of *G. microsporum* immunomodulatory protein gene according to the preferred embodiment of the present invention; wherein:

The arrows in FIG. 2A indicate the used primers, wherein 0821GW-R1 and 0821 GW-R2 were used in 5' genome walking;

FIG. 3 shows the 5' genome walking results of *G. microsporum* immunomodulatory protein gene according to the preferred embodiment of the present invention, which used 5'GW-R1/MKP24 in the first amplification and 5'GW-R2/MKP24 for the second amplification, wherein:

The boxes in FIG. 3B indicate the patented fragments of GMI sequence;

FIG. 5 shows the results of recombinant proteins, reLZ-8 and reGMI, in various concentrations of imidazole wash buffer performing affinity column purification according to the preferred embodiment of the present invention, wherein:

DESCRIPTION OF THE PREFERRED EMBODIMENTS

Hereinafter, the components and preferred embodiments according to the present invention will be described in detail with reference to the accompanying figures:

Materials

Please refer to Table 1, Table 2, and Table 3 for the strains, plasmids and primers used in according to the present invention, wherein the *Ganoderma microsporum* RSH 0821 used in the present invention is kept in the slant mediums of Potato dextrose agar (PDA) made by Difco, Detroit, Mich. at 25° C., while the hetero-expression system used the *Pichia pastoris* expression kit made by Invitrogen, Carlsbad, Calif., US. *Escherichia coli* JM109 was the host cell for plasmid operation and preservations according to the preferred embodiment of the present invention, while the common cultivation used plate solid medium of LB, Luria-Bertani agar by Alpha Bioscience, Baltimore or liquid medium of LB broth, wherein the cultivation temperature was at 37° C. and the liquid medium was shaken at 250 rpm. The strain was preserved in LB broth with 25% glycerine at −80° C.

TABLE 1

| Strain | Characteristics | Source |
|---|---|---|
| *Ganoderma* spp. | | |
| *G. microsporum* RSH 0821 | Heterokaryote, the source of gmi gene | This laboratory |
| *G. tsugae* RSH 1109 | Heterokaryote, the source of lz-8 gene | This laboratory |
| *E. coli* | | |
| JM109 | Plasmids construction and storage, recA1, supE44, endA1, hsdR17, gyrA96, relA1, thiΔ(lac-proAB), F' [traD36, proAB+, lacIq, lacZΔM15] | Stratagene (La Jolla, CA) |

TABLE 1-continued

| Strain | Characteristics | Source |
|---|---|---|
| Rosetta origami B (DE3) | Expression host, F⁻, ompT, hsdSB($r_B^-$, $m_B^-$), gal, dcm, lacY1, aphC, gor522::Tn10, trxB, pRARE(Cam$^R$, Kan$^R$, Tet$^R$) | Novagen (San Diego, CA) |
| *P. pastoris* | | |
| KM71 | Expression host, Mut$^s$, his4, AOX1::ARG4, arg4 | Invitrogen (Carlsbad, CA) |

TABLE 2

| Plasmid | Characteristics | Source |
|---|---|---|
| *E. coli* | | |
| YT&A | TA cloning vector, lacZ, Amp$^r$ | Yeastern (Taipei, Taiwan) |
| pGEM-T | TA cloning vector, lacZ, Amp$^r$ | Promega (Madison, WI, USA) |
| pGEX-4T-1 | Expression vector, tac promoter, lacI$^q$, Amp$^r$, GST-tag at N-terminal | Amersham Pharmacia (Uppsala, Sweden) |
| pGEXL | pGEX-4T-1 with lz-8 gene inserted at BamHI/EcoRI site | This study |
| *P. pastoris* | | |
| pPICZαA | Expression vector, AOX1 promoter, Zeo$^r$, α-factor signal peptide, c-myc epitope, His-tag at C-terminal | Invitrogen (Carlsbad, CA, USA) |
| PPLZ | pPICZαA with lz-8 gene inserted at EcoRI/XbaI site | This study |
| pPGMI | pPICZαA with gmi gene inserted at EcoRI/XbaI site | This study |

TABLE 3

| Primer | Sequence (5' → 3')ᵃ | Reference or Source |
|---|---|---|
| LZ8-F | TCCGACACTGCCTTGATCTTCAGG (SEQ ID NO:11) | This study |
| LZ8-R | GTTCCACTGGGCGATGATGAAGTC (SEQ ID NO:12) | This study |
| LZ8-BF | GGATCCATGTCCGACACTGCCT (SEQ ID NO:13) | This study |
| LZ8-ER | GAATTCCTAGTTCCACTGGGCGA (SEQ ID NO:14) | This study |
| LZ8-EF | GAATTCATGTCCGACACTGCC (SEQ ID NO:15) | This study |
| LZ8-XR | TCTAGATAGTTCCACTGGGCG (SEQ ID NO:16) | This study |
| 3'GW-F | CGTTCGACTACACCCCGAACTGGGGC (SEQ ID NO:17) | This study |
| MKP22 | GCGCTGCAGGCATGCGAGCTCCCAAGCTTGATCG (SEQ ID NO:18) | |
| MKP23 | AATTCGATCAAGCTTGGGAGCTCGCATGCCTGCAGCGC (SEQ ID NO:19) | |
| MKP24 | GCGCTGCAGGCATGCGAGCTG (SEQ ID NO:20) | |
| 0821GW-R1 | GAATTCGATGGCCCGCCGAGC (SEQ ID NO:21) | This study |
| 0821GW-R2 | CCCTTCTAGTTCCACTGGGCAAC (SEQ ID NO:22) | This study |
| GMI-XR | TCTAGATAGTTCCACTGGGCA (SEQ ID NO:23) | This study |

ᵃ The restriction enzyme cutting sites in primers are marked in bold font, BamH I: GGATCC, EcoR I: GAATTC, HindIII: AAGCTT, Xba I: TCTAGA Immunomodulatory Protein Gene Cloned from *Ganoderma microsporum*

Extraction of *Ganoderma microsporum* Chromosome DNA:

Referring to the method developed by Al-Samarrai and Schmid, the mycelium of *Ganoderma microsporum* was transferred to PDB liquid medium by the way of mass inoculation method and cultivated at 25° C. for one to several weeks, then the mycelium was collected through suction filtration method and washed by distilled water for several times. After removing water, the mycelium was instantly frozen in liquid nitrogen and grounded into powders, and preserved in −20° C. refrigerator.

Polymerase Chain Reaction (PCR) Analysis

The chromosomal DNA of *Ganoderma microsporum* as was used as a template and LZ8-F/LZ8-R as primer (Table 3) to perform PCR amplification, wherein the annealing temperature (Ta) was 48~60° C., elongation time ($t_e$) was 30 sec, and the nucleotide fragment was obtained through purification, connected to preserved plasmid yT&A by TA ligation method, and transformed to *E. coli* JM109 (Table 1) before the DNA sequencing analysis.

Genome Walking:

Referring to the method developed by Kilstrup and Kristiansen, restriction enzymes was used to cut chromosomal DNA into small fragments, adaptors with known sequences were connected to both ends of the DNA fragment, and then the gene specific primers and the specific primers on the adaptors were used to perform PCR amplification reaction and obtained a large number of target gene fragments. The primers used in Genome walking and the PCR conditions as shown in Table 4.

Hetero-Expression of *Ganoderma lucidum* Immunomodulatory Protein LZ-8 in *E. coli*

Establishment of pGEXL Expression Vectors:

Used the lz-8 gene obtained through PCR and preserved in yT&A as template and LZ8-BF and LZ8-ER with the cutting sites of BamH I and EcoR I as primers to perform the PCR amplification (Ta=60° C., $t_e$=30 sec). The obtained fragments were preserved in yT&A, cut and connected to the relative positions of pGEX-4T. The resultant vector was named pGEXL and then transformed into *E. coli* Rosetta-gami B (RGB) for expression.

Expression of *E. coli* Fusion Protein:

1% overnight cultivated strain was inoculated to 900 ml LB liquid medium with 100 μg/ml ampicillin, shaken and incubated at 37° C. until $OD_{600}$=0.6, and induced by 0.5 mM IPTG (isopropyl-D-thiogalacto-pyranoside) overnight at 30° C. Centrifugation (3000 g, 10 min., 4° C.) was used to collect mycelium and, after suspending in 5 ml phosphate buffer saline PBS (140 m M NaCl, 2.7 mM KCl, 10 mM $Na_2HPO_4$, 1.8 mM $KH_2PO_4$, pH 7.3), ultrasonication was used for cell disruption. Triton X-100 of final concentration 1% was added to increase the solubility of fusion proteins and the crude extract. After centrifugation (14000 g, 20 min., 4° C.), the supernatant was taken to perform the Glutathione Sepharose 4B affinity column purification to obtain fusion proteins for the rabbit polyclonal antibody production.

Hetero-Expression of *Ganoderma* Immunomodulatory Protein, in *P. pastoris*

Establishment of pPLZ and pPGMI Expression Vectors:

LZ-8 and the immunomodulatory protein gene, gmi gene, cloned from *G. microsporum* were used to perform PCR

TABLE 4

| | | PCR conditions | |
|---|---|---|---|
| Template DNA[a] | Primer[b] | Ta (° C.)[c] | $t_e$ (min.)[d] |
| 3' partial sequence walking | | | |
| 0821/EcoRI, 0821/HindIII | 3'GW-R/MKP24 | 54, 56, 58, 60 | 2 |
| 5' complete sequence walking | | | |
| 0821/EcoRI, 0821/HindIII | 1st PCR 0821GW-R1/MKP24 | 60 | 3 |
| | 2nd PCR 0821GW-R2/MKP24 | 56 | 2 |

[a]chromosome DNA cut by restriction enzyme.
[b]referring to Table 3.
[c]Ta = annealing temperature.
[d]$t_e$ = elongation time.

Figure 1A:
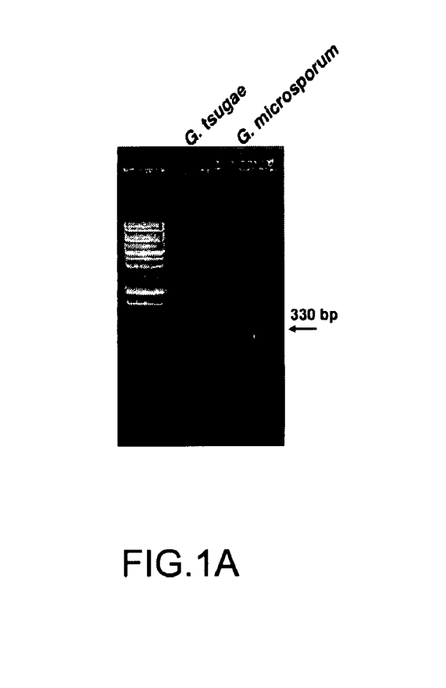
FIG. 1A shows the electrophoresis results of amplification fragment.
Figure 1B:
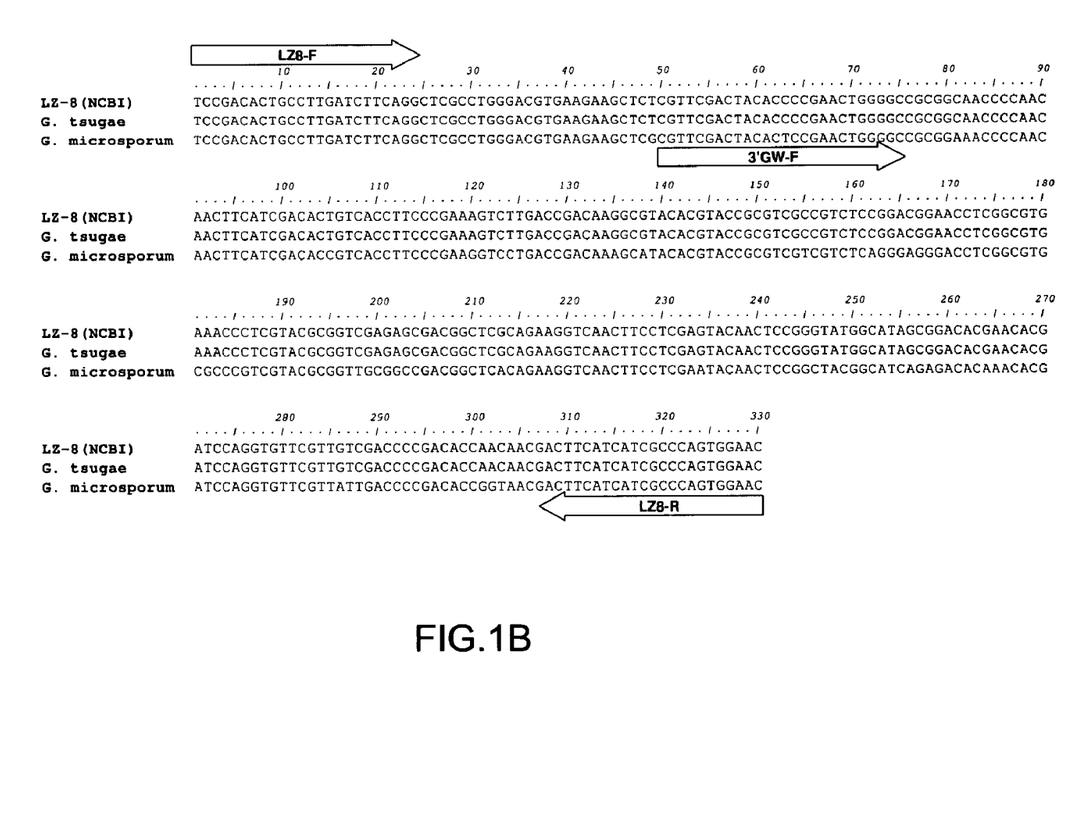
FIG. 1B shows the sequencing results of amplification fragment and an alignment between LZ-8 (NCBI; SEQ ID NO:4), the insert from G. Tsugae (SEQ ID NO: 5) and the insert from *G. microsporum* (SEQ ID NO:6)
Figure 2A:
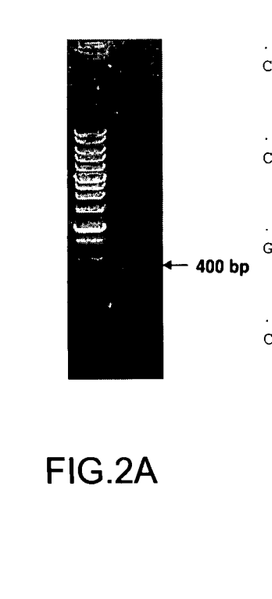
FIG. 2A shows the electphoresis results after amplification.
Figure 2B:
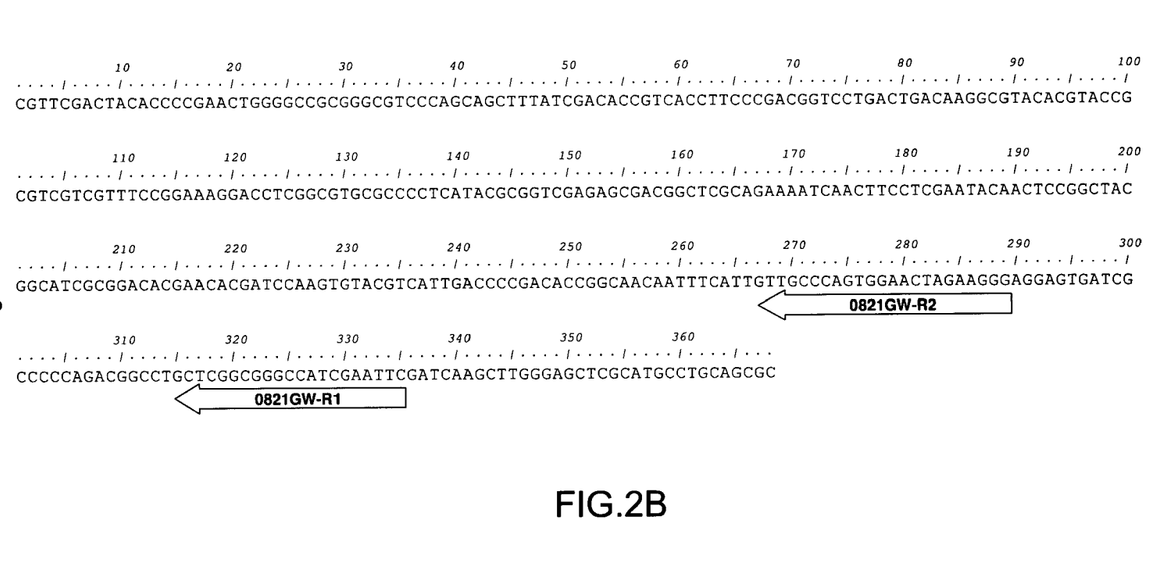
FIG. 2B shows the fragment sequence results (SEQ ID NO:7) of template DNA performing PCR amplification by using primers 3'GW-F/MKP24.
Figure 3A:
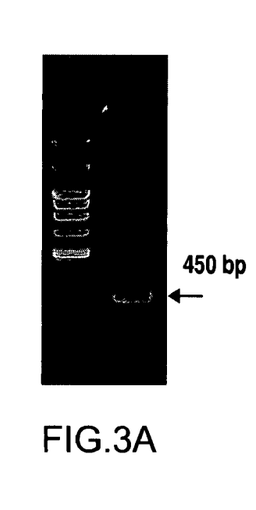
FIG. 3A shows the electrophoresis results after amplification.
Figure 3B:
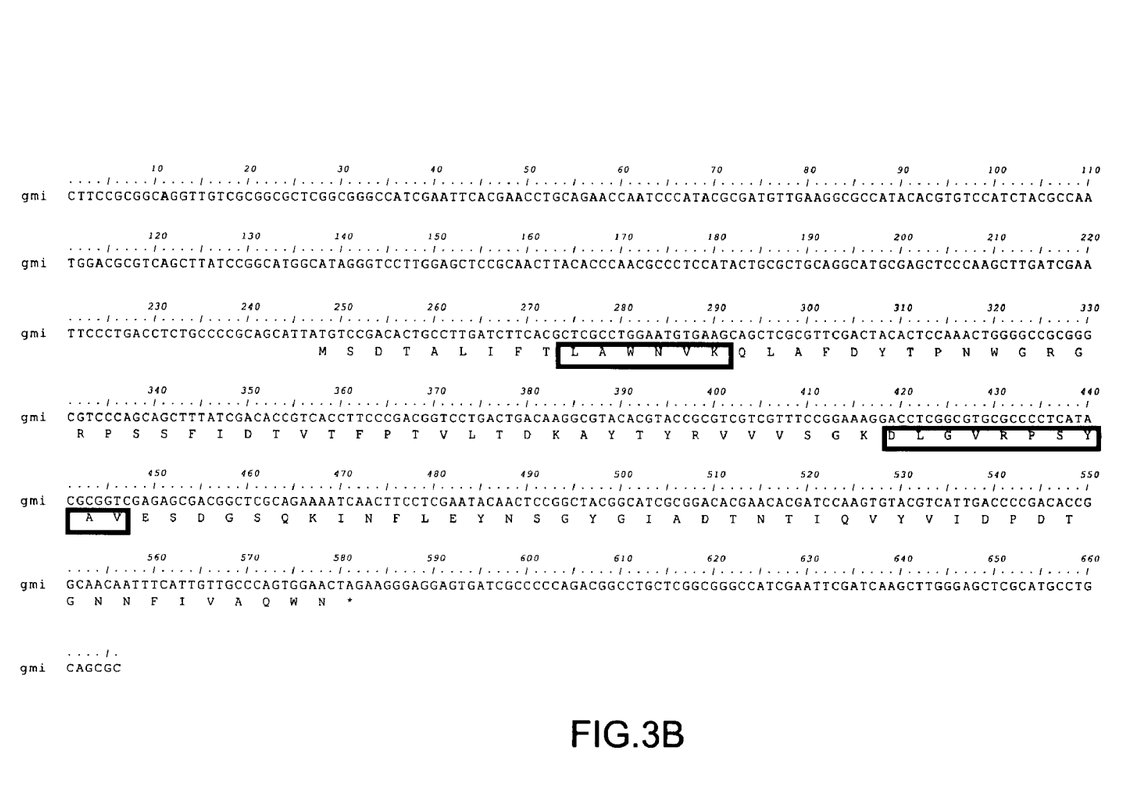
FIG. 3B shows the sequencing results of amplification fragment, and also the full sequence of *G. microsporum* immunomodulatory protein gene, gmi (polynucleotide sequence SEQ ID NO:1; amino acid sequence SEQ ID NO:8)
Figure 6:
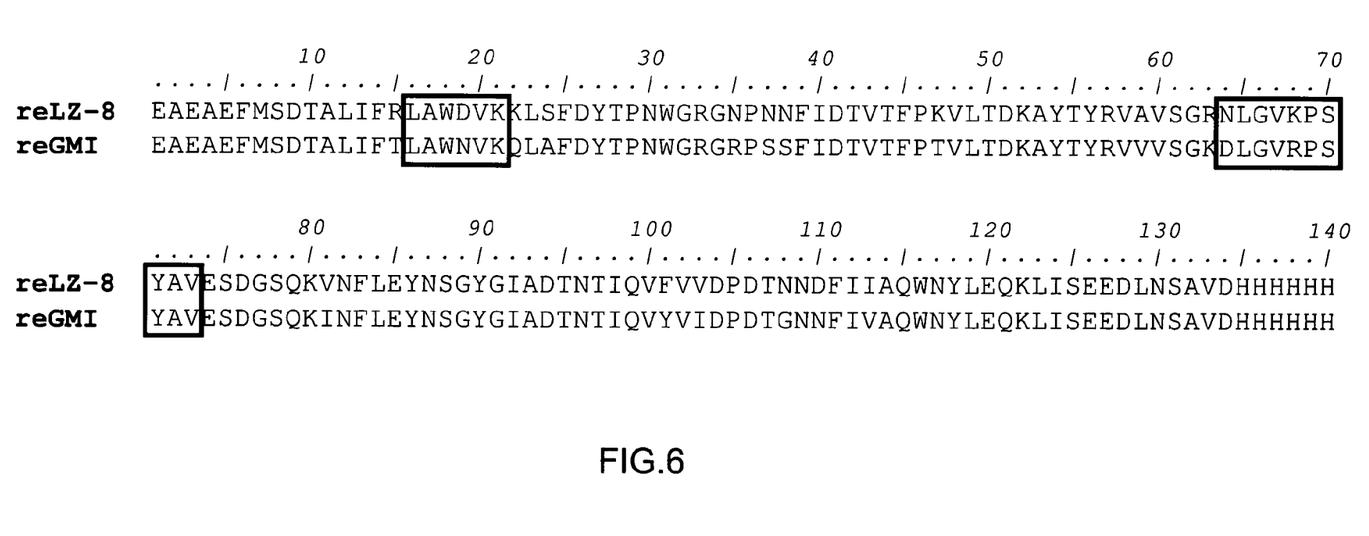
FIG. 6 shows the amino acid sequences of LZ-8 (SEQ ID NO:9) and GMI (SEQ ID NO: 10) recombinant proteins, reLZ-8 and reGMI, according to the preferred embodiment of the present invention, wherein the boxes indicate the patented fragments of LZ-8 sequence.

Results:

By using LZ-8 primer, the partial sequence of the immunomodulatory protein gene cloned from *G. microsporum* through PCR analysis was around 330 bp (FIG. 1). According to the known sequence of this new gene, a specific primer, 3'GW-F, was designed to perform the 3' genome walking to obtain the 3' end of unknown sequences of the new gene (FIG. 2). In order to clone the full gene of the new immunomodulatory protein at one time, at the 3' end of known sequences, two specific primers, 0821W-R1 and 0821GW-R2, were designed (Table 3) to perform the 5' genome walking so as to obtain a gene fragment of around 450 bp in length (FIG. 3A). Combining the 3' end of previously cloned gene sequence fragments, the full length of the new *G. microsporum* immunomodulatory protein gene was 666 bp and was named as gmi (FIG. 3B)

amplifications by using LZ8-EF/LZ8-XR and LZ8-EF/GMI-XR primers with the cut sites of restriction enzymes, EcoR I/Xba I (Table 3), respectively, and the obtained fragments were preserved in pGEM-T, cut and connect to the relative positions of pPICZ as to obtain expression vectors pPLZ and pPGMI. These expression vectors allowed the N-terminal of the target protein having α-factor signal peptide and the C-terminal having c-myc epitope and His-tag. When the recombinant protein was secreted out of the cells, signal peptide was cut to form reGMI (FIG. 6).

*P. pastoris* Transformation by Electroporation:

Referring to the *Pichia* expression kit manual of Invitrogen Company and the transformation method published by Wu and Letchworth, *P. pastoris* KM71 was cultivated in 200 mL YPD (Yeast Peptone Dextrose) liquid medium at 30° C. until $OD_{600}$ (optical density) was about 1.0-2.0 (1 unit $OD_{600}$ is about 5×10⁷ cells/mL) before collecting cells through centrifugation and then suspended in 100-200 mL pretreatment buffer solution (100 mM $CH_3COOLi$), 10 mM DTT (dithiothreitol), 0.6 M sorbitol, and 10 mM Tris-HCl (pH 7.5) at room temperature for 30 minutes before collecting cells through centrifugation. The cells were washed with 1 mL iced 1 M sorbitol three times, and suspended in 1 mL iced 1 M sorbitol (~10¹⁰ cells/mL) to become the competent cells used for electroporation. After plasmid isolation, the plasmid was cut by SacI and 1 μg DNA (10 μL) was mixed with 80 μl of competent cells, transferred to 0.2 cm-cuvette (BTX) for an ice bath for 5 minutes, and used the ECM 630 Electro Cell Manipulator Electroporation System of BTX, San Diego, Calif. to perform the electroporation process under the conditions of 1.5 kV, 25 μF, 200Ω. It was put into 1 mL iced YPDS liquid medium (1% yeast extract, 2% peptone, 2% dextrose, and 1 M sorbitol) right after electroporation to sit at 30° C. for 1-2 hours and then spread the yeast suspension onto the YPDS plate medium with 100 μg/ml zeocin (antibiotic) for cultivation at 30° C. Generally speaking, the higher resistance of antibiotics for the transformants, the higher expression of the recombinant proteins (Baneyx 2004).

Figure 4:
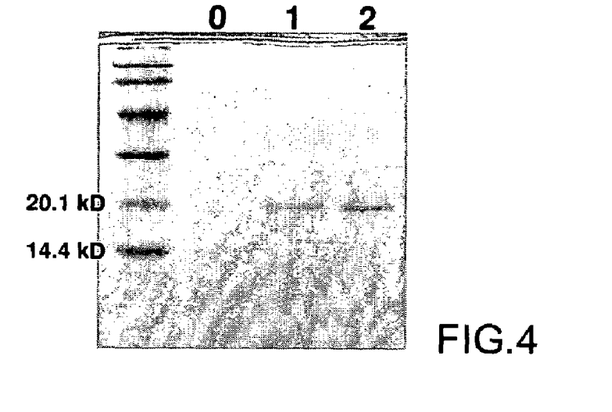
FIG. 4 shows the *G. microsporum* immunomodulatory protein GMI performing hetero-expression through PICZαA/ *Pichia pastoris* KM71 according to the preferred embodiment of the present invention.

Expression of *P. pastoris* Fusion Protein:

After cultivating and activating the transformants twice in BMGY liquid medium with 100 μg/ml zeocin (1% yeast extract, 2% peptone, 100 mM potassium phosphate with pH 6, 1.34% YNB, 4×10⁻⁵% biotin, and 1% glycerol) at 30° C., cells at the stationary phase were inoculated into 500 ml BMGY so the final $OD_{600}$ to be 0.1. After 24 hours of cultivation, change the culture medium to 100 ml BMMY liquid medium (1% yeast extract, 2% peptone, 100 mM potassium phosphate with pH 6, 1.34% YNB, 4×10⁻⁵% biotin, and 0.5% MeOH) to induce the fusion protein expression, and MeOH (methanol) was added every 24 hours until the final concentration to be 0.5%. After two days of induction, the supernatant of the culture was used for SDS-PAGE analysis. Results are shown in FIG. 4. Under the induction of 0.5% MeOH, the protein concentration of recombinant protein reGMI increased with the increasing time of induction.

Figure 5A:
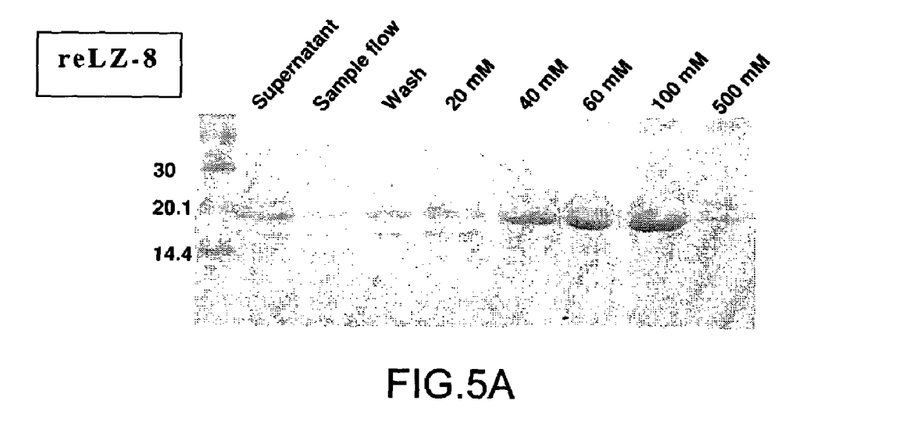
FIG. 5A is reLZ-8.
Figure 5B:
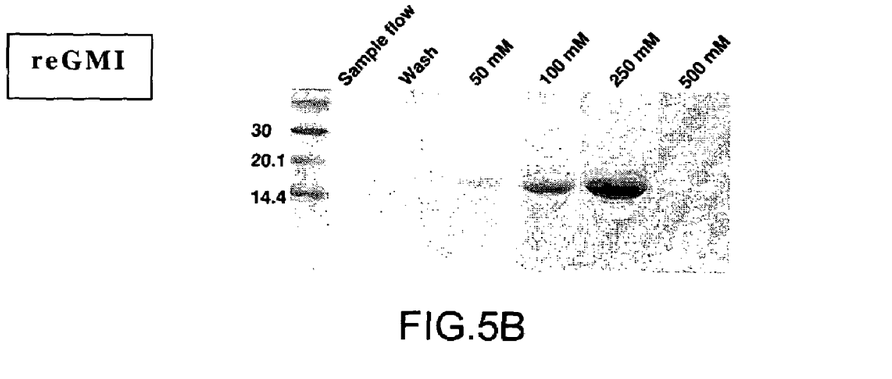
FIG. 5B is reGMI.

Purification of *P. pastoris* Fusion Protein:

Ten times of colloidal volume of wash buffer (50 mM $NaH_2PO_4$, 300 mM NaCl, 10 mM imidazole, pH 7.4) was used to wash Ni-NTA column. After loading sample, ten times of colloidal volume of wash buffer was used to wash the non-specific absorbent proteins, and at last flushed down the fusion proteins with phosphate buffer in various imidazole concentrations, wherein reLZ-8 at 40~100 mM and reGMI at 100~250 mM, respectively (FIG. 5). After the purified fusion proteins were dialyzed by PBS, they were preserved in solution or in dry powders at 4° C. Although there was almost no other proteins found in the supernatant of *P. pastoris* culture except the target proteins, the affinity column purification was able to eliminate the pigments in the supernatant and reduced the interference factors during the immunomodulatory activity assay of recombinant proteins.

Characteristic Analysis of *P. pastoris* Fusion Protein

Figure 7:
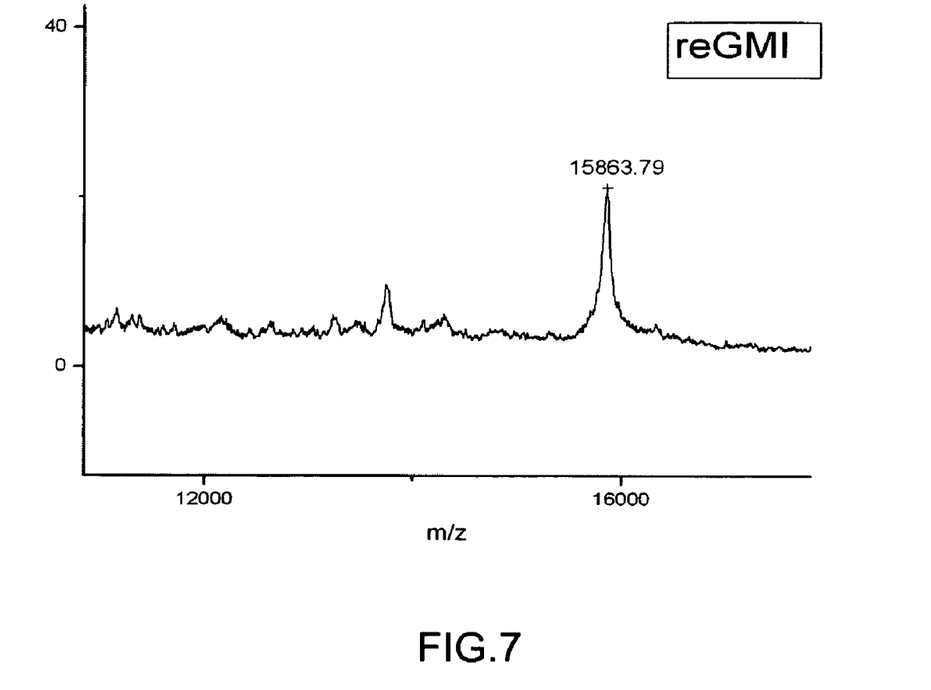
FIG. 7 shows the MALDI-TOF analysis results of reGMI according to the preferred embodiment of the present invention.

Molecular Weight and Glycosylation Modification Analysis:

Regardless of recombinant proteins reLZ-8 and reGMI, their theoretical molecular weights can be derived from known sequences, but the molecular weights of these recombinant proteins shown on the electrophoresis films were larger than their theoretical molecular weights. In order to obtain more accurate molecular weights, reGMI underwent a MALDI-TOF (Matrix Assisted Laser Desorption/Ionization-Time Of Flight) mass spectrography analysis and the results are shown in FIG. 7. The molecular weight of reGMI determined by MALDI was 15863.79 Da, almost the same as the theoretical value, 15847.47 Da. The SDS-PAGE would overestimate the molecular weights under the Tris buffer system. In addition, the MALDI-TOF results showed that no glycosylation modification was found for reGMI expressed in *P. pastoris*.

Figure 8:
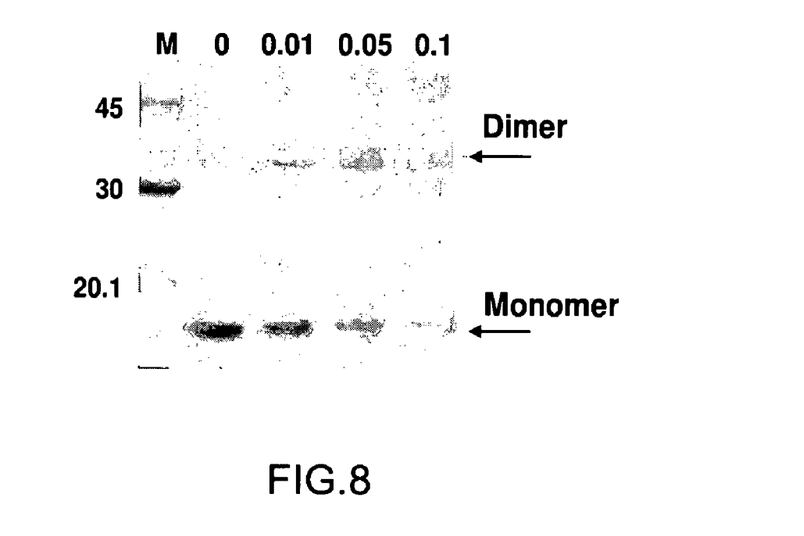
FIG. 8 shows the crosslinking figure of reGMI in various concentrations of glutaraldehyde according to the preferred embodiment of the present invention.

Homodimer Analysis:

Native LZ-8 existed in the form of homodimer and the physiology activity of FIP-gts with the same amino acid sequence as LZ-8 was closely related to the form of homodimer. In order to investigate whether the native recombinant protein reGMI expressed by *P. pastoris* can exist in the form of homodimer, the chemical crosslinking in various glutaraldehyde concentrations was performed. Glutaraldehyde is able to make the lysines on protein surfaces to form covalent bonds with each other so that the various proteins with nearby spatial positions have the chance to connect and fasten to each other. The experiment results is shown in FIG. 8. Under the effect of 0.01% glutaraldehyde, the signals of reGMI homodimer began to appear and, as the concentration of glutaraldehyde increased, the percentage of homodimer increased, indicating that the native reGMI existed in the form of homodimer.

Protein Configuration Analysis:

As indicated by the boxes in FIG. 6, the two partial amino acid sequences of LZ-8 under the patent protection are (1)-Leu-Ala-Trp-Asp-Val-Lys-(LAWDVK; SEQ ID NO:24) and (2)-Asn-Leu-Gly-Val-Lys-Pro-Ser-Tyr-Ala-Val-(NLGVKPSYAV; SEQ ID NO: 25);

The amino acid sequences, similar to the regions of LZ-8 applied for patent, of GMI cloned from *G. microsporum* are (1)-Leu-Ala-Trp-Asn-Val-Lys-(LAWNVK; SEQ ID NO:2) and (2)-Asp-Leu-Gly-Val-Arg-Pro-Ser-Tyr-Ala-Val-(DLGVRPSYAV; SEQ ID NO:3).

Figure 9:
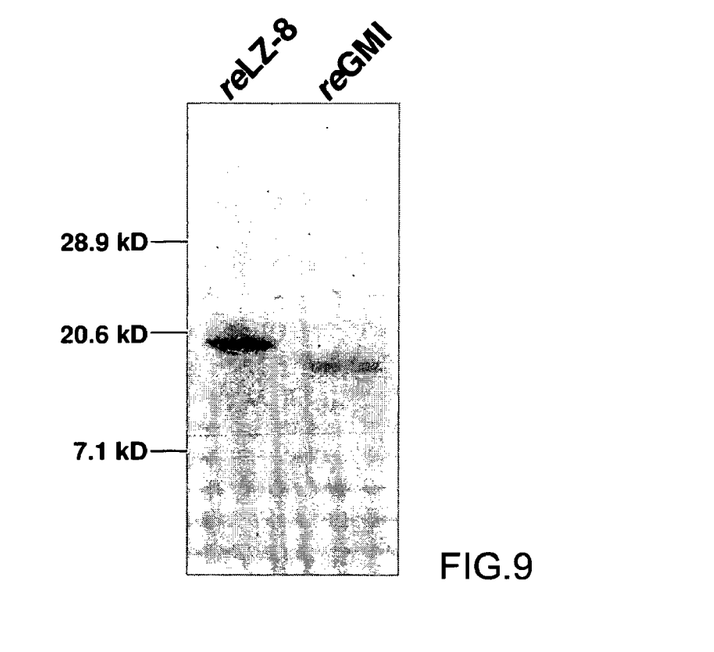
FIG. 9 shows the results of equal amounts of reLZ-8 and reGMI performing the Western hybridization analysis according to the preferred embodiment of the present invention.

GMI is significantly difference from the patented amino acid sequence of LZ-8, and the differences of these amino acids may cause the changes of protein configuration and then bring about the differences of physiological activities. In order to investigate the differences in configurations of reGMI and reLZ-8, both proteins were performed Western hybridization analysis and the results showed that reGMI could be recognized by the antibodies of LZ-8 but the signal was a little bit weaker (FIG. 9), revealing that reGMI and LZ-8 had similar structure. The differences in sequences of reGMI led certain degree of difference in structure from reLZ-8 and said difference would affect the immunomodulatory activity. Therefore, through the following immunomodulatory activity test, it was able to understand the effects of the amino acid differences to their immunomodulatory activities.

Immunomodulatory Activity Test

Purified reGMI was used to stimulate the dendritic cells for the immunomodulatory activity test and the procedures are listed as followings:

5~6 weeks old BALB/c mice bone marrow cells were cultivated in RPMI-1640 culture medium with 10% FCS (Fetal Calf Serum); IL-4 and GMCSF (granulocyte/macrophage colony stimulating factor) was added at the second day to facilitate the cell differentiation. Macrophages were removed by transferring to the new culture plate for continue cultivation at the fourth day. Various concentrations of protein samples were added into the six-day-old immature dentritic cells and the crude extract collected after 20 hours for the ELISA (Enzyme-linked immunosobent assay) measurement of IL-12.

Purified reGMI was used to stimulate macrophages and T cells for the immunomodulatory activity test and the procedures are listed as followings:

Macrophages J774A.1 and human T cell line Jurkat cells were cultivated separately in RPMI-1640 culture medium with 10% FCS. Various concentrations of protein samples were added and crude extracts were collected 6 hours later for the ELISA measurement of TNF-α and IL-2.

Figure 10:
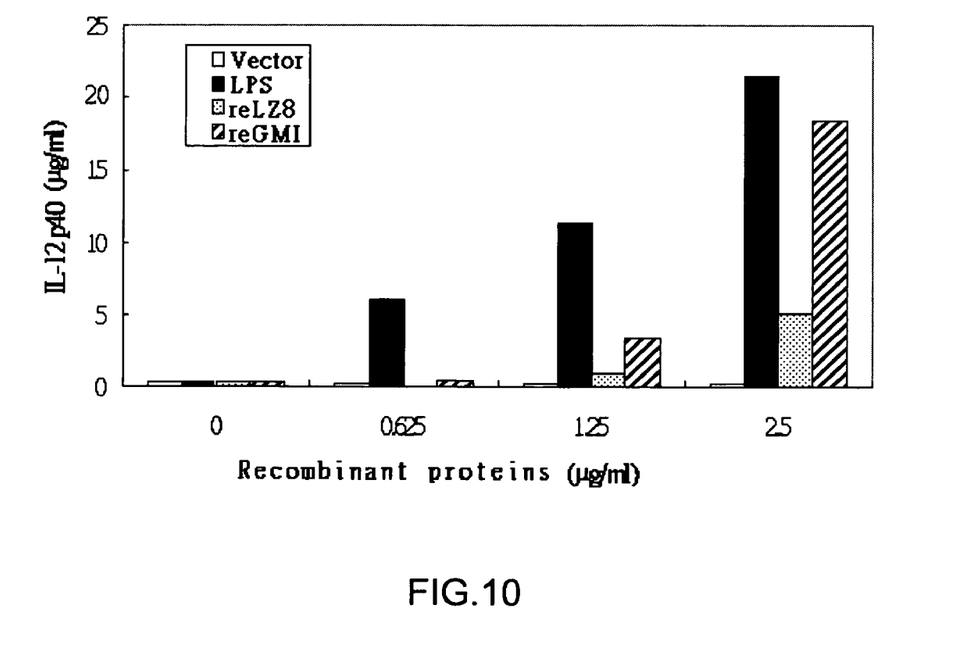
FIG. 10 shows the results of reGMI promoting BALB/c mice bone marrow dendritic cells to secrete IL-12p40 according to the preferred embodiment of the present invention.
Figure 11:
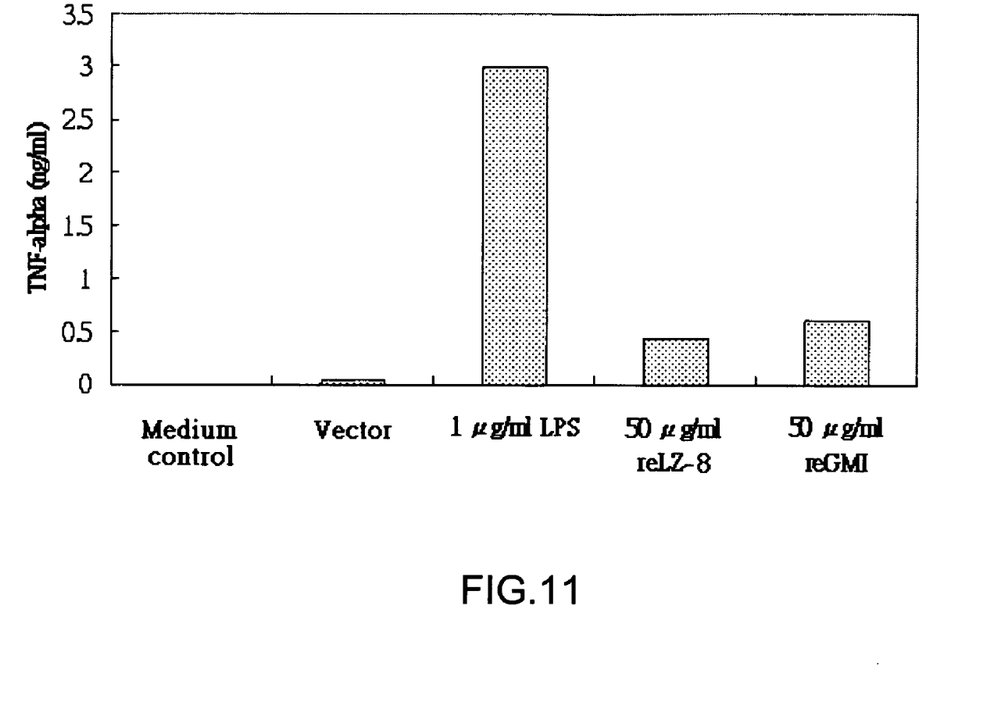
FIG. 11 shows the results of reGMI promoting mice macrophages, J774A.1, to secrete TNF-α according to the preferred embodiment of the present invention.
Figure 12:
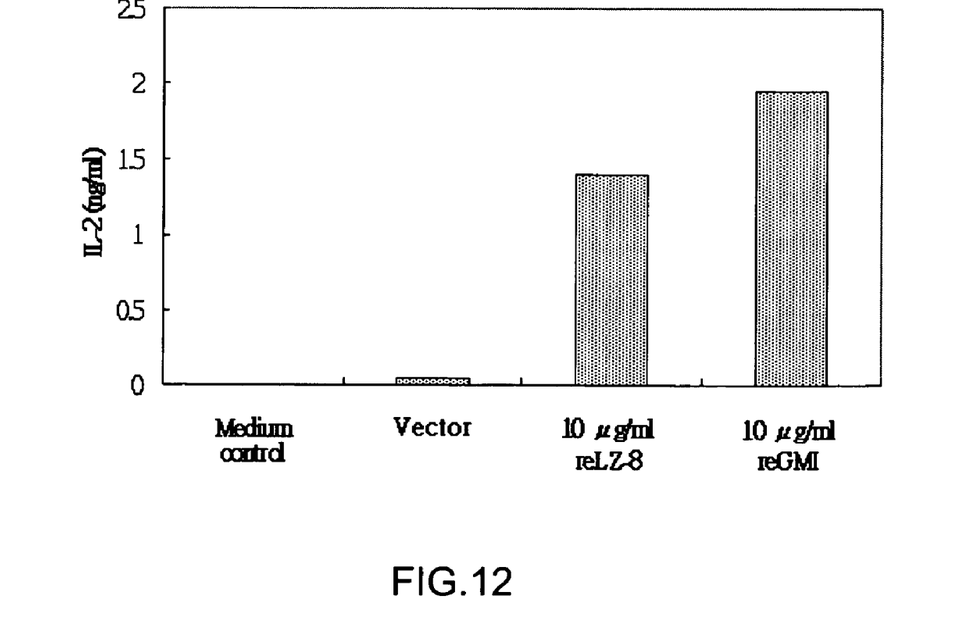
FIG. 12 shows the results of reGMI promoting human T cell line Jurkat cells to secrete L-2 according to the preferred embodiment of the present invention.

Results:

In order to eliminate the possibilities of P. pastoris cell wall component interferences, the pPICZαA of P. pastoris KM71 was expressed, purified and dialyzed under the same conditions described above. The vector without expressive genes was used as the negative control group (FIG. 10~FIG. 12), wherein, regardless in BALB/c mice bone marrow dendritic cells, macrophage J447A.1, or Jurkat cells, no induced immune response was found. Four concentrations of purified reLZ-8 and reGMI of 0, 0.625, 1.25, and 2.5 µg/ml were applied to BALB/c mice bone marrow dendritic cells and all were able to stimulate cells to secrete IL-12 p40, wherein reGMI under 2.5 µg/ml stimulated dendritic cells to secrete six times the amount of IL-12p40 than the same concentration of reLZ-8 (FIG. 10). IL-12p40 was one subunit of IL-12, wherein the increase of IL-12p40 expression meant that the expression of IL-12 might increase as well. IL-12 was the important cell endocrine that dendritic cells activated or even maintained $T_H1$ immune cell population, while the existence of IL-12 would also suppress the growth and differentiation of $T_H2$ cells. *Ganoderma* or lingzhi immunomodulatory proteins could be directly applied to T cells, as shown in FIG. 12 which 10 µg/ml of reLZ-8 and reGMI were applied in human T cell line Jurkat and both could activate cells to secrete IL-2 (Interleukin). IL-2 could facilitate the un-differentiated T cells to proliferate and differentiate. In addition, IL-2 was one of the cell endocrines secreted by $T_H1$ cell. TNF-α (tumor necrosis factor) was one of the cell endocrines for macrophage to induce the inflammation reaction and also one of the indices to determine whether macrophage was activated. As shown in FIG. 11, both reLZ-8 and reGMI were able to activate mice macrophage J774A.1 to secrete TNF-α under 50 µg/ml concentration.

From the abovementioned immune activity tests, it was able to know that the immunomodulatory protein reGMI according to the present invention not only had the ability to promote the activations of all kinds of cells and also had better immunomodulatory efficiency than that of reLZ-8.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

I claim:

1. An isolated protein comprising the amino acid sequence as identified by SEQ ID NO:8.

2. The protein of claim 1, wherein said protein is encoded by a polynucleotide comprising the coding sequence from nucleotide position 247 to 580 of SEQ ID NO:1.

3. The protein of claim 2, wherein said polynucleotide is derived from *Ganoderma microsporum* RSH 0821.

4. The protein of claim 1, wherein said protein has a molecular weight of 15863.79 Da by Matrix Assisted Laser Desorption/Ionization-Time Of Flight (MALDI-TOF) analysis.

5. The protein as set forth in claim 1, wherein the protein exists as a homodimer.

6. The protein of claim 1 consisting of the amino acid sequence as identified by SEQ ID NO:8.

* * * * *

UNITED STATES PATENT AND TRADEMARK OFFICE
CERTIFICATE OF CORRECTION

PATENT NO. : 7,601,808 B2  Page 1 of 1
APPLICATION NO. : 11/365881
DATED : October 13, 2009
INVENTOR(S) : Tsai-Leng Lin It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (303) days Delete the phrase "by 303 days" and insert -- by 404 days --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,808 B2 | Page 1 of 1 |
| APPLICATION NO. | : 11/365881 | |
| DATED | : October 13, 2009 | |
| INVENTOR(S) | : Tsai-Leng Lin | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 404 days.

Signed and Sealed this

Twenty-first Day of December, 2010

David J. Kappos
*Director of the United States Patent and Trademark Office*

SEQUENCE LISTING

<160> NUMBER OF SEQ ID NOS: 3

<210> SEQ ID NO 1
<211> LENGTH: 666
<212> TYPE: DNA
<213> ORGANISM: Ganoderma microsporum

<400> SEQUENCE: 1

```
cttccgcggc aggttgtcgc ggcgctcggc gggccatcga attcacgaac ctgcagaacc      60
aatcccatac gcgatgttga aggcgccata cacgtgtcca tctacgccaa tggacgcgtc     120
agcttatccg gcatggcata gggtccttgg agctccgcaa cttacaccca acgccctcca     180
tactgcgctg caggcatgcg agctcccaag cttgatcgaa ttccctgacc tctgccccgc     240
agcattatgt ccgacactgc cttgatcttc acgctcgcct ggaatgtgaa gcagctcgcg     300
ttcgactaca ctccaaactg gggccgcggg cgtcccagca gctttatcga caccgtcacc     360
ttcccgacgg tcctgactga caaggcgtac acgtaccgcg tcgtcgtttc cggaaaggac     420
ctcggcgtgc gcccctcata cgcggtcgag agcgacgcct cgcagaaaat caacttcctc     480
gaatacaact ccggctacgg catcgcggac acgaacacga tccaagtgta cgtcattgac     540
cccgacaccg gcaacaattt cattgttgcc cagtggaact agaagggagg agtgatcgcc     600
cccagacggc ctgctcggcg ggccatcgaa ttcgatcaag cttgggagct cgcatgcctg     660
cagcgc                                                                666
```

<210> SEQ ID NO 2
<211> LENGTH: 6
<212> TYPE: PRT
<213> ORGANISM: Ganoderma microsporum

```
-continued

<400> SEQUENCE: 2

Leu Ala Trp Asn Val Lys
1               5

<210> SEQ ID NO 3
<211> LENGTH: 10
<212> TYPE: PRT
<213> ORGANISM: Ganoderma microsporum

<400> SEQUENCE: 3

Asp Leu Gly Val Arg Pro Ser Tyr Ala Val
1               5                   10
```